US008601882B2

(12) United States Patent
Gray et al.

(10) Patent No.: US 8,601,882 B2
(45) Date of Patent: Dec. 10, 2013

(54) IN SITU TESTING OF MECHANICAL PROPERTIES OF CEMENTITIOUS MATERIALS

(75) Inventors: Dennis Gray, Comanche, OK (US);
Joseph Maxson, Duncan, OK (US);
James Heathman, Katy, TX (US);
Sairam Pindiprolu, Vijayawada (IN);
Flint R. George, Flower Mound, TX (US); Melissa Allin, Comanche, OK (US); Keith Blaschke, Duncan, OK (US)

(73) Assignee: Halliburton Energy Sevices, Inc., Houston, TX (US)

( * ) Notice: Subject to any disclaimer, the term of this patent is extended or adjusted under 35 U.S.C. 154(b) by 447 days.

(21) Appl. No.: 12/390,242

(22) Filed: Feb. 20, 2009

(65) Prior Publication Data

US 2011/0061525 A1 Mar. 17, 2011

(51) Int. Cl.
*G01N 3/10* (2006.01)

(52) U.S. Cl.
USPC .......................................................... 73/803

(58) Field of Classification Search
USPC .......................................................... 73/803
See application file for complete search history.

(56) References Cited

U.S. PATENT DOCUMENTS

| | | |
|---|---|---|
| 2,662,827 A | 12/1953 | Clark |
| 3,541,845 A | 11/1970 | Kierkegaard-Hansen |
| 3,574,281 A | 4/1971 | Casey et al. |
| 3,619,463 A | 11/1971 | Budin et al. |
| 3,779,085 A | 12/1973 | Rice |
| 4,138,892 A | 2/1979 | Davis |
| 4,259,868 A | 4/1981 | Rao et al. |
| 4,377,087 A | 3/1983 | Rodot |
| 4,389,896 A | 6/1983 | Babcock |
| 4,408,489 A | 10/1983 | Spangle |
| 4,430,889 A | 2/1984 | Sutton |
| 4,487,056 A | 12/1984 | Wiley |
| 4,491,017 A | 1/1985 | Iyler |
| 4,538,452 A | 9/1985 | Hrvojic |
| 4,567,759 A | 2/1986 | Ekstrom et al. |
| 4,567,765 A | 2/1986 | Rao et al. |
| 4,607,530 A | 8/1986 | Chow |

(Continued)

FOREIGN PATENT DOCUMENTS

| | | |
|---|---|---|
| DE | 86 01 833 | 1/1987 |
| EP | 0 124 383 A1 | 11/1984 |

(Continued)

OTHER PUBLICATIONS

Dillenbeck, R.L., GoBoncan, V., and Rogers, M.J., "Testing Cement Static Tensile Behavior Under Downhole Conditions," SPE 97967, Society of Petroleum Engineers, Copyright 2005, 12 pages.

(Continued)

*Primary Examiner* — F. Daniel Lopez
(74) *Attorney, Agent, or Firm* — John Wustenberg; Fish & Richardson P.C.

(57) ABSTRACT

A system for measuring one or more physical properties of cementitious material is operable to cure a slurry of cementitious material under desired conditions of temperature and pressure. Particularly, the system may be operable to cure the slurry under a temperature and pressure expected to be experienced downhole. The system may also be used to determine properties of the cured cementitious material, such as maximum yield strength and shear bond strength at the desired temperature and pressure. The desired conditions of temperature and pressure may be applied both during curing and testing of the cementitious material.

12 Claims, 4 Drawing Sheets

(56) References Cited

U.S. PATENT DOCUMENTS

| | | |
|---|---|---|
| 4,648,264 A | 3/1987 | Freese et al. |
| 4,685,092 A | 8/1987 | Dumont |
| 4,691,558 A | 9/1987 | Vinson et al. |
| 4,703,427 A | 10/1987 | Catala et al. |
| 4,757,479 A | 7/1988 | Masson et al. |
| 4,809,237 A | 2/1989 | Vogel et al. |
| 4,823,594 A | 4/1989 | Gray |
| 4,848,145 A | 7/1989 | Blaschke et al. |
| 4,893,285 A | 1/1990 | Masson et al. |
| 4,896,303 A | 1/1990 | Leslie et al. |
| 4,970,695 A | 11/1990 | Huau |
| 5,009,512 A | 4/1991 | Lessi et al. |
| 5,036,709 A | 8/1991 | McRae |
| 5,089,989 A | 2/1992 | Schmidt et al. |
| 5,127,473 A | 7/1992 | Harris et al. |
| 5,216,638 A | 6/1993 | Wright |
| 5,233,863 A | 8/1993 | Surjaatmadja et al. |
| 5,248,200 A | 9/1993 | Walsh |
| 5,325,723 A | 7/1994 | Meadows et al. |
| 5,346,012 A | 9/1994 | Heathman et al. |
| 5,353,637 A | 10/1994 | Plumb et al. |
| 5,368,103 A | 11/1994 | Heathman et al. |
| 5,377,160 A | 12/1994 | Tello et al. |
| 5,377,753 A | 1/1995 | Haberman et al. |
| 5,389,706 A | 2/1995 | Heathman et al. |
| 5,412,990 A | 5/1995 | D'Angelo et al. |
| 5,487,307 A | 1/1996 | Landgren et al. |
| 5,488,994 A | 2/1996 | Laurel et al. |
| 5,544,704 A | 8/1996 | Laurel et al. |
| 5,571,951 A | 11/1996 | Jamth |
| 5,572,021 A | 11/1996 | Heathman et al. |
| 5,696,059 A | 12/1997 | Onan et al. |
| 5,712,431 A | 1/1998 | Vilendrer |
| 5,718,292 A | 2/1998 | Heathman et al. |
| 5,741,971 A | 4/1998 | Lacy |
| 5,763,773 A | 6/1998 | Birchak et al. |
| 5,783,822 A | 7/1998 | Buchanan et al. |
| 5,787,983 A | 8/1998 | Heathman et al. |
| 5,836,200 A | 11/1998 | Belonenko et al. |
| 5,869,750 A | 2/1999 | Onan et al. |
| 5,964,293 A | 10/1999 | Chatterji et al. |
| 5,968,255 A | 10/1999 | Mehta et al. |
| 5,969,059 A | 10/1999 | Murai et al. |
| 5,972,103 A | 10/1999 | Mehta et al. |
| 5,992,223 A | 11/1999 | Sabrins et al. |
| 5,996,693 A | 12/1999 | Heathman |
| 6,019,835 A | 2/2000 | Chatterji et al. |
| 6,053,245 A | 4/2000 | Haberman |
| 6,055,874 A | 5/2000 | Onan et al. |
| 6,060,434 A | 5/2000 | Sweatman et al. |
| 6,070,662 A | 6/2000 | Ciglenec et al. |
| 6,112,599 A | 9/2000 | Maki, Jr. |
| 6,124,246 A | 9/2000 | Heathman et al. |
| H1932 H | 1/2001 | Heathman et al. |
| 6,170,575 B1 | 1/2001 | Reddy et al. |
| 6,209,646 B1 | 4/2001 | Reddy et al. |
| 6,227,039 B1 | 5/2001 | Te'eni |
| 6,227,294 B1 | 5/2001 | Chatterji et al. |
| 6,245,142 B1 | 6/2001 | Reddy et al. |
| 6,258,757 B1 | 7/2001 | Sweatman et al. |
| 6,269,684 B1 | 8/2001 | Maki, Jr. et al. |
| 6,270,565 B1 | 8/2001 | Heathman |
| 6,345,535 B1 | 2/2002 | Sabins et al. |
| 6,367,549 B1 | 4/2002 | Chatterji et al. |
| 6,367,550 B1 | 4/2002 | Chatterji et al. |
| 6,379,456 B1 | 4/2002 | Heathman et al. |
| 6,444,316 B1 | 9/2002 | Reddy et al. |
| 6,454,001 B1 | 9/2002 | Thompson et al. |
| 6,478,868 B1 | 11/2002 | Reddy et al. |
| 6,478,869 B2 | 11/2002 | Reddy et al. |
| 6,484,568 B1 | 11/2002 | Griffith et al. |
| 6,494,951 B1 | 12/2002 | Reddy et al. |
| 6,510,743 B2 | 1/2003 | McAfee et al. |
| 6,527,051 B1 | 3/2003 | Reddy et al. |
| 6,527,438 B2 | 3/2003 | Zollinger et al. |
| 6,547,871 B2 | 4/2003 | Chatterji et al. |
| 6,554,071 B1 | 4/2003 | Reddy et al. |
| 6,591,910 B1 | 7/2003 | Chatterji et al. |
| 6,595,068 B2 | 7/2003 | Brovold et al. |
| 6,610,139 B2 | 8/2003 | Reddy et al. |
| 6,644,402 B1 | 11/2003 | Sharma et al. |
| 6,655,213 B1 | 12/2003 | Reinhardt et al. |
| 6,660,080 B2 | 12/2003 | Reddy et al. |
| 6,762,156 B2 | 7/2004 | Heathman et al. |
| 6,767,867 B2 | 7/2004 | Chatterji et al. |
| 6,782,735 B2 | 8/2004 | Walters et al. |
| 6,789,621 B2 | 9/2004 | Wetzel et al. |
| 6,797,054 B2 | 9/2004 | Chatterji et al. |
| 6,817,238 B2 | 11/2004 | Go Boncan et al. |
| 6,818,596 B1 | 11/2004 | Hayes |
| 6,828,922 B1 | 12/2004 | Gremmert et al. |
| 6,829,922 B2 | 12/2004 | Patin et al. |
| 6,834,233 B2 | 12/2004 | Economides et al. |
| 6,843,846 B2 | 1/2005 | Chatterji et al. |
| 6,874,353 B2 | 4/2005 | Johnson et al. |
| 6,892,814 B2 | 5/2005 | Heathman et al. |
| 6,910,535 B2 | 6/2005 | Tare et al. |
| 6,918,292 B2 | 7/2005 | Go Boncan et al. |
| 6,951,249 B1 | 10/2005 | Chatterji et al. |
| 6,964,302 B2 | 11/2005 | Luke et al. |
| 6,978,835 B1 | 12/2005 | Reddy et al. |
| 6,994,164 B2 | 2/2006 | Tare et al. |
| 7,004,256 B1 | 2/2006 | Chatterji et al. |
| 7,008,477 B2 | 3/2006 | Chatterji et al. |
| 7,013,975 B2 | 3/2006 | Chatterji et al. |
| 7,048,054 B2 | 5/2006 | Heathman et al. |
| 7,089,816 B2 | 8/2006 | Hakimuddin |
| 7,096,944 B2 | 8/2006 | Vargo, Jr. et al. |
| 7,128,142 B2 | 10/2006 | Heathman et al. |
| 7,128,149 B2 | 10/2006 | Heathman et al. |
| 7,143,827 B2 | 12/2006 | Chatterji et al. |
| 7,178,590 B2 | 2/2007 | Vargo, Jr. et al. |
| 7,191,663 B2 | 3/2007 | Go Boncan et al. |
| 7,240,545 B1 | 7/2007 | Jennings |
| 7,244,303 B2 | 7/2007 | Chatterji et al. |
| 7,255,170 B2 | 8/2007 | Chatterji et al. |
| 7,284,898 B2 | 10/2007 | Duell et al. |
| 7,285,166 B2 | 10/2007 | Luke et al. |
| 7,296,927 B2 | 11/2007 | Reddy et al. |
| 7,325,629 B2 | 2/2008 | Blaschke et al. |
| 7,373,982 B2 | 5/2008 | Brothers et al. |
| 7,380,466 B2 | 6/2008 | Deeg |
| 7,549,320 B2 | 6/2009 | Funkhouser et al. |
| 7,552,648 B2 | 6/2009 | McMechan et al. |
| 2001/0001381 A1 | 5/2001 | Reddy et al. |
| 2001/0037687 A1 | 11/2001 | Brovold |
| 2003/0140707 A1 | 7/2003 | Pyle et al. |
| 2003/0150263 A1 | 8/2003 | Economides et al. |
| 2003/0161211 A1 | 8/2003 | Duell et al. |
| 2003/0221829 A1 | 12/2003 | Patel et al. |
| 2004/0054262 A1 | 3/2004 | Horak |
| 2004/0055392 A1 | 3/2004 | Patin et al. |
| 2004/0154263 A1 | 8/2004 | Li et al. |
| 2004/0221990 A1 | 11/2004 | Heathman et al. |
| 2004/0226483 A1 | 11/2004 | Chatterji et al. |
| 2005/0009710 A1 | 1/2005 | Heathman et al. |
| 2005/0080161 A1 | 4/2005 | Tare et al. |
| 2005/0109507 A1 | 5/2005 | Heathman et al. |
| 2005/0126300 A1 | 6/2005 | Go Boncan et al. |
| 2005/0135185 A1 | 6/2005 | Duell et al. |
| 2005/0152432 A1 | 7/2005 | Hakimuddin |
| 2005/0204960 A1 | 9/2005 | Heathman et al. |
| 2006/0000612 A1 | 1/2006 | Reddy et al. |
| 2006/0225523 A1 | 10/2006 | Reddy et al. |
| 2006/0258545 A1 | 11/2006 | Chatterji et al. |
| 2007/0012441 A1 | 1/2007 | Heathman et al. |
| 2007/0082822 A1 | 4/2007 | Kirsner et al. |
| 2007/0105995 A1 | 5/2007 | Chatterji et al. |
| 2007/0169937 A1 | 7/2007 | Allin et al. |
| 2007/0173412 A1 | 7/2007 | Allin et al. |
| 2008/0168848 A1 | 7/2008 | Funkhouser et al. |
| 2008/0178683 A1 | 7/2008 | Heathman et al. |
| 2008/0197605 A1 | 8/2008 | Blaschke et al. |

(56) References Cited

U.S. PATENT DOCUMENTS

| | | | |
|---|---|---|---|
| 2009/0084189 A1 | 4/2009 | McMechan et al. | |
| 2011/0061525 A1 | 3/2011 | Gray et al. | |
| 2011/0094295 A1 | 4/2011 | Meadows et al. | |

FOREIGN PATENT DOCUMENTS

| | | |
|---|---|---|
| EP | 0 176 400 B1 | 4/1986 |
| EP | 0 176 408 B1 | 4/1986 |
| EP | 0 101 580 B1 | 12/1986 |
| EP | 0 110 750 B1 | 9/1988 |
| EP | 0 098 778 B1 | 3/1989 |
| EP | 0 198 985 B1 | 12/1989 |
| EP | 0 443 936 A1 | 8/1991 |
| EP | 0 395 499 B1 | 7/1993 |
| EP | 0 865 612 B1 | 6/2002 |
| EP | 1 541 987 | 6/2005 |
| FR | 2 340 551 | 9/1977 |
| GB | 2 353 546 A | 2/2001 |
| GB | 2 354 026 A | 3/2001 |
| GB | 2 355 742 A | 5/2001 |
| GB | 2 386 625 A | 9/2003 |
| WO | WO 00/49273 | 8/2000 |
| WO | WO 2004/008302 A1 | 10/2004 |
| WO | WO 2005/065400 | 7/2005 |

OTHER PUBLICATIONS

Minear, John W. and Goodwin, K. Joe, "*Cement-Sheath Evaluation*," Chapter 10, Petroleum Well Construction, John Wiley & Sons Publisher, ISBN 0-471-96938-9, copyright 1998, front and back cover and pp. 271-296.

Love, A.E.H., "*A Treatise on the Mathematical Theory of Elasticity*," Fourth Edition, Dover Publications, New York, 1944, pp. 144-145.

Thiercelin, J.J., et al., "*Cement Design Based on Cement Mechanical Response,*" SPE Drilling & Completion, Society of Petroleum Engineers, SPE 52890, Dec. 1998, pp. 266-273.

Goodwin, K.J., "*Cement Sheath Stress Failure*," SPE Drilling Engineering, SPE 20453, Dec. 1992, pp. 291-296, and additional pp. 501-508 from SPE 20453.

Deeg, Wolfgang, et al., "*How Foamed Cement Advantages Extend to Hydraulic Fracturing Operations*," World Oil, Nov. 1999, pp. 51-53.

FlexiForce®, materials downloaded from Tekscan website (www.tekscan.com) on FlexiForce® sensors), http://www.tekscan.com/flexiforce.html, visited Aug. 3, 2005, 20 pages.

Bridgman, P. W., "*V. Breaking Tests Under Hydrostatic Pressure and Conditions of Rupture*", Philosophical Magazine and Journal of Science, vol. 24, Sixth Series, pp. 63-80, (1912).

Clayton, N., "*Fluid-pressure Testing of Concrete Cylinders,*" Magazine of Concrete Research, vol. 30, No. 102, pp. 26-30, (1978).

Clayton, N. et al., "*The Diphase Concept, With Particular Reference to Concrete*", Developments in Concrete Technology, vol. 1, F. D. Lydon, Ed.; Applied Science Publisher Ltd, Chapter 7, pp. 283-318, (1979).

Richart, Frank E. et al., "A Study of the Failure of Concrete Under Combined Compressive Stresses", The University of Illinois—Engineering Experiment Station, Bulletin No. 185, pp. 3-253, (1928).

Mindess, S. et al., "The Nitrogen Gas Tension Test of Concrete", Proceedings of ConMat '05 and Mindess Symposium, Aug. 22-24, 2005, The University of British Columbia, Vancouver, Canada, 8 pages, (2005).

Timonen, Tuomo, "International Search Report" PCT/GB2008/000031, mailed Apr. 2, 2008, 3 pages.

"Standard Test Method for Tensile Strength of Hydraulic Cement Mortars", ASTM Standards, C-190-85, pp. 197-202.

Sabins, Fred, "MMS Project Long-Term Integrity of Deepwater Cement Systems Under Stress/Compaction Conditions", CSI Technologies, Sep. 3, 2004.

Gary Funkhouser et al., "Measuring Cement Properties" U.S. Appl. No. 11/622,255, filed Jan. 11, 2007 (25 pages).

Wolfgang F. J. Deeg, "Apparatus and Method for Determining Mechanical Properties of Cement for a Well Bore" U.S. Appl. No. 11/206,719, filed Aug. 18, 2005 (32 pages).

David Leon Meadows et al., "Cement Testing" U.S. Appl. No. 12/607,560, filed Oct. 28, 2009 (33 pages).

David Leon Meadows et al., "Cement Testing" U.S. Appl. No. 13/542,011, filed Jul. 5, 2012 (31 pages).

David Leon Meadows et al., "Cement Testing" U.S. Appl. No. 13/409,745, filed Mar. 1, 2012 (43 pages).

IN SITU TESTING OF MECHANICAL PROPERTIES OF CEMENTITIOUS MATERIALS

TECHNICAL FIELD

This disclosure relates to a system for measuring one or more physical properties of cementitious material. The system may be operable to cure a slurry of cementitious material under desired conditions of temperature and pressure. Particularly, the system may be operable to cure the slurry under a temperature and pressure expected to be experienced downhole. The system may also be used to determine properties of the cured cementitious material, such as maximum yield strength and shear bond strength at the desired temperature and pressure. The desired conditions of temperature and pressure may be applied both during curing and testing of the cementitious material.

BACKGROUND

Some wellbores, for example, those of some oil and gas wells, are lined with a casing. The casing stabilizes the sides of the wellbore.

In a cementing operation, cement is introduced down the wellbore and into an annular space between the casing and the surrounding earth. The cement secures the casing in the wellbore, and prevents fluids from flowing vertically in the annulus between the casing and the surrounding earth.

Different cement formulations are designed for a variety of wellbore conditions, which may be above ambient temperature and pressure. In designing a cement formulation, a number of potential mixtures may be evaluated to determine their mechanical properties under various conditions.

SUMMARY

A first aspect is directed to an apparatus having a housing defining an interior chamber and a first piston adjacent a second piston in the interior chamber. An interstitial region may be formed between the first and second piston. The first piston and second piston may be moveable relative to each other in the interior chamber. An interior volume may be defined by the first piston and the second piston. The interior volume may have a central portion at a region proximate the interstitial region and enlarged portions at opposite ends of the first portion. The enlarged portions may be larger than a cross-section of the central portion.

A second aspect is directed to a device for curing and testing a cementitious material. The device may include an enclosure defining an interior chamber and a first piston disposed in the interior chamber. The first piston may have a first interior cavity comprising a narrow portion and an enlarged portion. A second piston may be disposed in the interior chamber adjacent the first piston at an interstitial region. The second piston may also include a second interior cavity having a narrow portion and an enlarged portion. The first piston and second piston may be moveable relative to each other in the interior chamber. The first interior cavity and second interior cavity may be arranged such that the narrow portions are adjacent and in fluid communication with each other at the interstitial region.

A third aspect is directed to a method of curing and testing a cementitious material under desired conditions of temperature and pressure. The method may include introducing a slurry of cementitious material into an interior volume defined by a first member and a second member, the first member and the second member moveable relative to each other, and applying a desired temperature and a desired pressure to the slurry as the slurry cures. The method may also include applying a fluid pressure to generate one of a shear stress or a tensile stress in the cured cementitious material while maintaining the cured cementitious material at the desired temperature and pressure.

One or more of the aspects may include one or more of the following features. A sleeve may be disposed in the central portion of the volume. The sleeve may include an interior passageway having a constant cross-section. A third piston may be disposed in the enlarged portion of the first piston or second piston and may be operable to move relative thereto in a longitudinal direction of the housing. A portion of the third piston may extend into the central portion of the interior volume. A first port opening may be included in the interior chamber proximate the interstitial region. The first port may be operable to introduce fluid pressure to the interstitial region to apply a separation force operable to separate the first piston and the second piston. A temperature control device operable to control a temperature of the interior chamber may be included. A second port may be operable to introduce fluid pressure into the interior chamber, and a pressure control device may be operable to control a pressure of the interior chamber by adjusting the fluid pressure introduced via the second port.

One or more of the aspects may also include one or more of the following features. A first opening may be defined in the enclosure proximate the interstitial region for introducing fluid pressure into the interior chamber. The fluid pressure may be operable to apply a separation force to the first piston and the second piston. A tubular member may be disposed in a central region defined by the aligned narrow portions of the first interior cavity and the second interior cavity, and the tubular member may include a constant cross-sectional interior passage. A third piston may be disposed in the enlarged portion of either of the first piston or second piston. The third piston may be moveable relative to either of the first piston or second piston in a longitudinal direction. The third piston may also extend into the narrow portion of either of the first piston or the second piston. A port may be formed in the enclosure and may be in communication with the interior chamber. The port may be adjacent the third piston and may be adapted to introduce fluid pressure to the third piston. A pressure control device may be operable to control a pressure of the enclosure by adjusting the fluid pressure introduced via a second opening in the enclosure. A temperature control device operable to control a temperature within the enclosure may be included.

One or more of the aspects may further include one or more of the following features. Introducing the slurry into the interior volume may include introducing the slurry into an interior volume defined by interior contours of a first member and a second member adjacent each other at an interstitial region. Applying a fluid pressure generate one of a shear stress or a tensile stress in the cured cementitious material while maintaining the cured cementitious material at the desired temperature and pressure may include applying the fluid pressure to a third member moveable relative to the first member to press the cured cementitious material relative to a cylindrical member in which the cured cementitious material is disposed. Applying a desired temperature and a desired pressure to the slurry as the slurry cures may include applying a temperature and a pressure expected to be experienced by the cementitious material downhole. A characteristic indicative of the tensile stress may be sensed. Further, applying a fluid pressure to generate one of a shear stress or a tensile stress in the cured cementitious material while maintaining the cured cementitious material at the desired temperature and pressure may include applying the fluid pressure to an interstitial region between the first member and the second member to apply a separation force to the first member and the second member.

The details of one or more implementations are set forth in the accompanying drawings and the description below. Other features, objects, and advantages will be apparent from the description and drawings, and from the claims.

DETAILED DESCRIPTION

Figure 1:
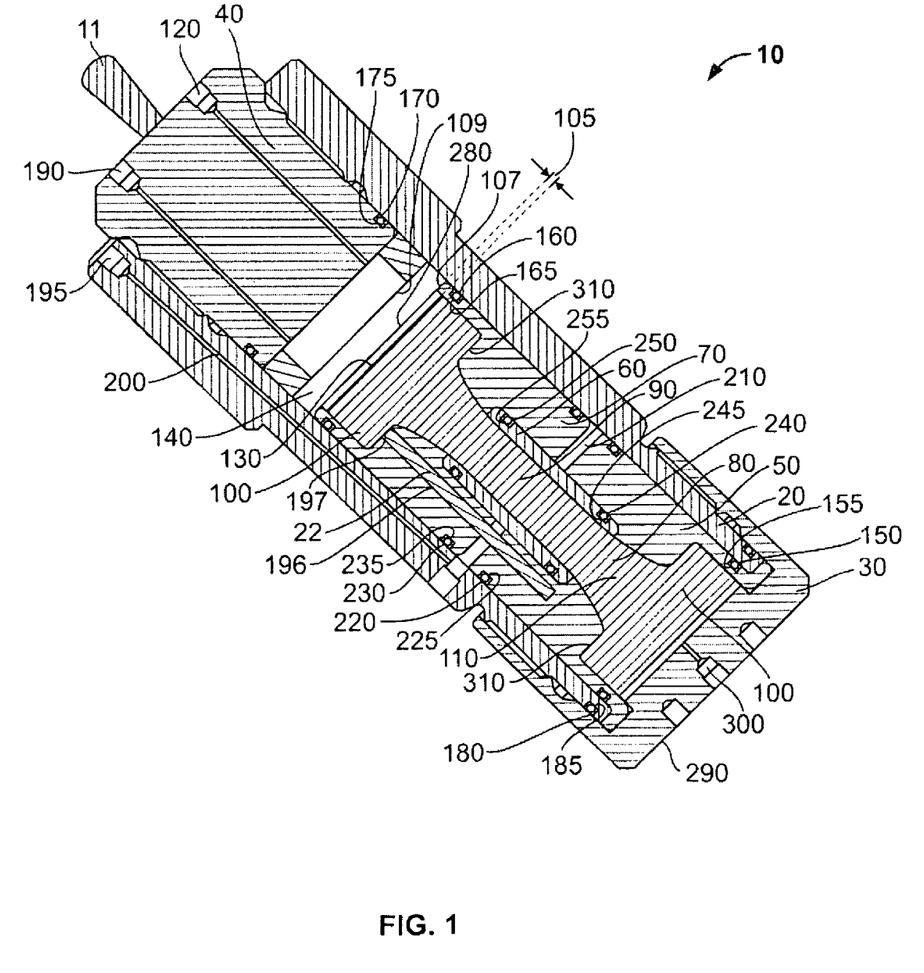
FIG. 1 is a cross-sectional view of an example system for curing and, optionally, testing cementitious materials under desired conditions of temperature and pressure.

FIG. 1 illustrates a system 10 for measuring one or more physical properties of cementitious material. As used herein, a cementitious material may include a liquid or semi-liquid mixture (hereinafter referred to as a "slurry") that cures or hardens over time. For example, a cementitious material may be a cement, a resin, a mixture of cement and resin, or a mixture having additional, fewer, or different components. Example cementitious materials may include cements, such as a Portland cement and compositions thereof having, for example, Pozzolans, silica, or non-cementitious materials such as resins, polymers, cross-linked polymers, in-situ polymerized products, ceramics, as well as others.

The system 10 may include a pressure vessel 20 with a first end-cap 30, a second end-cap 40, a first piston 50, a sleeve 60, and a second piston 70. A handle 11 may be coupled to the second end-cap 40. Interior contours of the first piston 50, sleeve 60, and the second piston 70 combine to form an interior volume 80. The interior volume 80 includes a central portion 90 disposed between opposing flange portions 100. According to some implementations, the central portion 90 and the flange portions 100 have circular cross-sectional shapes. Particularly, the central portion 90 may be a uniform cylinder having a constant diameter. The flange portions 100 may also be cylindrical. In some instances, the flange portions 100 have a diameter larger than the diameter of the central portion 90. In other instances, cross-sectional shapes of the central portion 90 and the flange portions 100 may be any suitable shape.

A slurry of the cementitious material may be introduced into the interior volume 80 at selected pressure and temperature and allowed to cure or solidify therein. In some instances, a gap 105 may be formed between surface 130 of the cementitious material and surface 107 of the second piston 70. The gap 105 may be defined such that, if any expansion of the cementitious material occurs during curing, the cementitious material would not extend beyond the surface 107 and potentially interfere with subsequent testing of the cementitious material. For example, during a subsequent tensile test, the solidified cementitious material would be prevented from contacting the surface 109 of a spacer ring 425. The spacer ring 425 may be formed from a material suitable to absorb large impact loads. For example, in some instances, the spacer ring 425 may be formed from any suitable high temperature elastomer or other high temperature polymers. For example, the spacer ring 425 may be formed from polytetrafluoroethylene (PTFE). Impact loads may be experienced when the sample 110 fractures, in which case the second piston 70 may rapidly move towards the second end-cap 40. Consequently, the second piston 70 may impact the spacer ring 425 and not the second end-cap 40 and, thus, avoid damaging either or both of the second piston 70 and second end-cap 40. When solidified, the cementitious material forms sample 110 having the shape of the interior volume 80, including the central portion 90 and the flange portions 100. The central portion 90 defined by an interior of the sleeve 60 may form a central region of the sample in the sample. The central portion 90 may be used to determine the mechanical properties of the cementitious material.

Within the system 10, the cementitious material may be cured at a desired temperature and/or pressure. For example, in some implementations, pressures may range from atmospheric pressure up to 20,000 psi or greater, and temperatures may range from below ambient temperature up to 500° F. In some implementations, for example, the pressures may be within the range of atmospheric pressure up to 60,000 psi. However, the pressures may be defined to be any desired pressure, particularly any pressure that may be expected to be experienced by the cementitious material downhole. Similarly, the temperatures may also be at any desired temperature, particularly, any temperature that may be experienced downhole. Pressure within the system 10 may be controlled by applying a hydraulic pressure via port 120 until a desired curing pressure is obtained. In some instances, the pressure may be applied by a fluid and maintained at a constant level using an external pump. An example pump may be one that is controlled to provide a constant pressure or volume, although any suitable pump may be used. Example fluids for applying the hydraulic pressure includes water, oil, any inert or near-inert gas, or any fluid or mixture of fluids (including gas or gases) expected to be encountered by the cementitious material downhole (hereinafter referred to as "fluid"). The fluid used to apply the hydraulic pressure may form a layer on one or more surfaces of the cementitious material, particularly surface 130.

A portion of the fluid may accumulate in a volume 140 adjacent to the surface 130. The fluid transmits hydraulic pressure to the volume of the cementitious material. The system 10 may be externally heated in any number of ways. For example, the system 10 may be heated by a heating jacket coupled to the system 10, by inserting the system 10 into an autoclave, by coupling (e.g., clamping) one or more heaters onto the system 10, or by any other method or apparatus to heat the system 10. In addition or alternately, the system 10 may be cooled. In some implementations, the system 10 may be cooled by insertion of the system 10 into a cooling chamber, by applying a cooling jacket to the system 10, by partially or completely immersing the system 10 into a cold water bath, or by any other method or apparatus to cool the system 10. The spacer ring 425, discussed in more detail below, may also be disposed in the volume 140.

The slurry of the cementitious material is allowed to cure under the conditions of the applied temperature and pressure. Once cured, the slurry of cementitious material forms the sample 110 having the shape of the interior volume 80. As explained above, the sample 110 includes the central portion 90 and flange portions 100. The sample 110 may also include merging radii 135 that blends the shapes of the central portions 90 and the flange portions 100 to substantially reduce or minimize stress concentrations in the sample 110 and provide improved testing consistency. The applied pressure and/or temperature may be set at any desired level, such as to simulate conditions existing downhole in a wellbore. Further, the pressure and/or temperature of the system may be changed over time in a desired manner. Altering the pressure and/or temperature while the slurry of cementitious material cures may simulate changing conditions expected to be experienced by the cementitious materials downhole. According to some implementations, control of the temperature and/or pressure may be performed by a controller connected to the one or more devices for heating, cooling, and/or applying pressure to the system 10. For example, a programmable controller may be coupled to a pump for applying the hydraulic pressure to the cementitious material, a heating mechanism, and/or a cooling mechanism to simulate downhole conditions expected to be experienced by the cementitious material. The controller may automatically alter the temperature and/or pressure conditions by controlling the respective devices according to a defined program as the slurry of cementitious material cures.

The system 10 may also include sealing members 150 and 160. The sealing member 150 may be disposed between the first piston 50 and the pressure vessel 20, and the sealing member 160 may be disposed between the second piston 70 and the pressure vessel 20. In some implementations, the sealing members 150, 160 are disposed in grooves 155, 165 formed in the first and second pistons, 50, 70. The sealing members 150, 160 are adapted to maintain hydraulic pressure applied to cementitious material as it cures, for example by preventing or substantially reducing the escape from the interior volume 80 of the fluid and pressure applied thereby. In some implementations, the sealing members 150, 160 may be O-rings or any other suitable sealing material or element.

A sealing member 170 may also be disposed between the second end-cap 40 and the pressure vessel 20, and a sealing member 180 may be disposed between pressure vessel 20 and the first end-cap 30. The sealing members 170, 180 are disposed in grooves 175, 185 formed in second end-cap 40 and pressure vessel 20, respectively. The sealing members 170 and 180 may be adapted to prevent or substantially reduce any pressure leakage out of the system 10 to the atmosphere. The sealing members 170, 180 may be O-rings or any other suitable sealing material or element. For example, some implementations may be used at temperatures in excess of failure temperatures of many polymeric seals. Accordingly, some implementations may utilize metal-to-metal seals.

A temperature within the system 10 may be monitored with a temperature monitoring device, such as a thermocouple, a resistance temperature detector (RTD) device, or other suitable device. The temperature monitoring device may be disposed in port 190. The temperature monitoring device may be coupled to the controller, described above, via a wire extending through the port 190 or via a wireless connection. Strain measurements may be obtained with one or more strain gauges. As shown in FIG. 1, a strain gauge 22 may be disposed in a channel 196, such as via a pass-through 197.

The system 10 is also operable to determine stress-strain characteristics and/or other mechanical properties of the cured sample 110. For example, the system 10 may be operable to perform a tensile test on the sample 110 to determine the stress-strain characteristics and/or mechanical properties. The tensile test may be performed by applying hydraulic pressure to the first and second pistons 50 and 70 which, in turn, apply pressure to the opposing flange portions 100 until the sample 110 fractures. Tensile loading may be applied to the sample 110 by pumping a fluid, such as the fluid used for applying hydraulic pressure to the cementitious material during curing, described above, through port 195. The fluid travels through a passageway 200 formed in the pressure vessel 20. In the implementation shown in FIG. 1, the passageway 200 provides communication with an interior of the pressure vessel 20 and an exterior of the system 10. However, any other suitable passageway providing communication with the interior of the pressure vessel 20 may be used. For example, in other implementations, a passageway extending radially through the pressure vessel 20 may be used. The pumped fluid pressurizes an interstitial region 210 between the first piston 50 and the second piston 70.

The system 10 may also include a sealing member 220 disposed between the first piston 50 and the pressure vessel 20 near the interstitial region 210, and a sealing member 230 disposed between the second piston 70 and the pressure vessel 20 near the interstitial region 210. The sealing members 220 and 230 may be disposed in grooves 225, 235 formed in an exterior surface of the first and second pistons 50, 70, respectively. The sealing members 220, 230 may be O-rings or any other suitable sealing material or element. Additionally, sealing members 240, 250 may also be included. The sealing member 240 may be disposed between the first piston 50 and the sleeve 60, and the sealing member 250 may be disposed between the second piston 70 and the sleeve 60. The sealing members 240, 250 may be retained in grooves 245, 255 formed in the sleeve 60. The sealing members 220-250 cooperate to retain the pressurized fluid in the interstitial region 210.

The pressurized fluid applied through the port 195 and passageway 200 works to separate the first and second pistons 50, 70. The first and second pistons 50, 70 contact respective flange portions 100 and transmit the separating force thereto, creating tensile stress in the sample 110. As shown in FIG. 1, the first piston 50 is clamped within the pressure vessel 20 against the first end-cap 30. As the first piston 50 is clamped in place, the second piston 70 moves towards an interior surface of the second end-cap 40, placing the sample 110 in tension. In other implementations, the first piston 50 may be freely moveable within the pressure vessel 20. In such instances, the first piston 50 moves towards and contacts an interior surface of the first end-cap 30. When the first piston 50 and the first end-cap 30 contact, the first piston 50 remains stationary, and the pressurized fluid works to move the second piston 70 toward the interior surface of the second end-cap 40, placing the sample 110 in tension.

As the fluid pressure is increased, the tensile force applied to the sample 110 is also increased, which, in turn, increases the tensile stress within the sample 110. The shape of the specimen may be designed to ensure that the mechanical properties under consideration can be studied in a uniform section, which is the central portion 90 of the sample. The internal contours of the first and second pistons 50, 70 may be shaped to minimize the stress concentrations elsewhere in the sample 110. Thus, when the tensile stress in the sample 110 exceeds the strength of the cured cementitious material, the sample 110 is designed to break in the central portion 90 having a uniform cross-sectional area. The maximum tensile stress experienced by the sample 110 before fracturing would be a true indication of the tensile strength of the cementitious material. Therefore, the system 10 is operable to determine a maximum tensile strength of cementitious material under conditions, e.g., temperature and pressure, that would be experienced downhole. The reproduced downhole conditions may be applied to the cementitious material while curing and maintained while the sample 110 is subjected to experimentation, e.g., the applied tensile loading.

Figure 2:
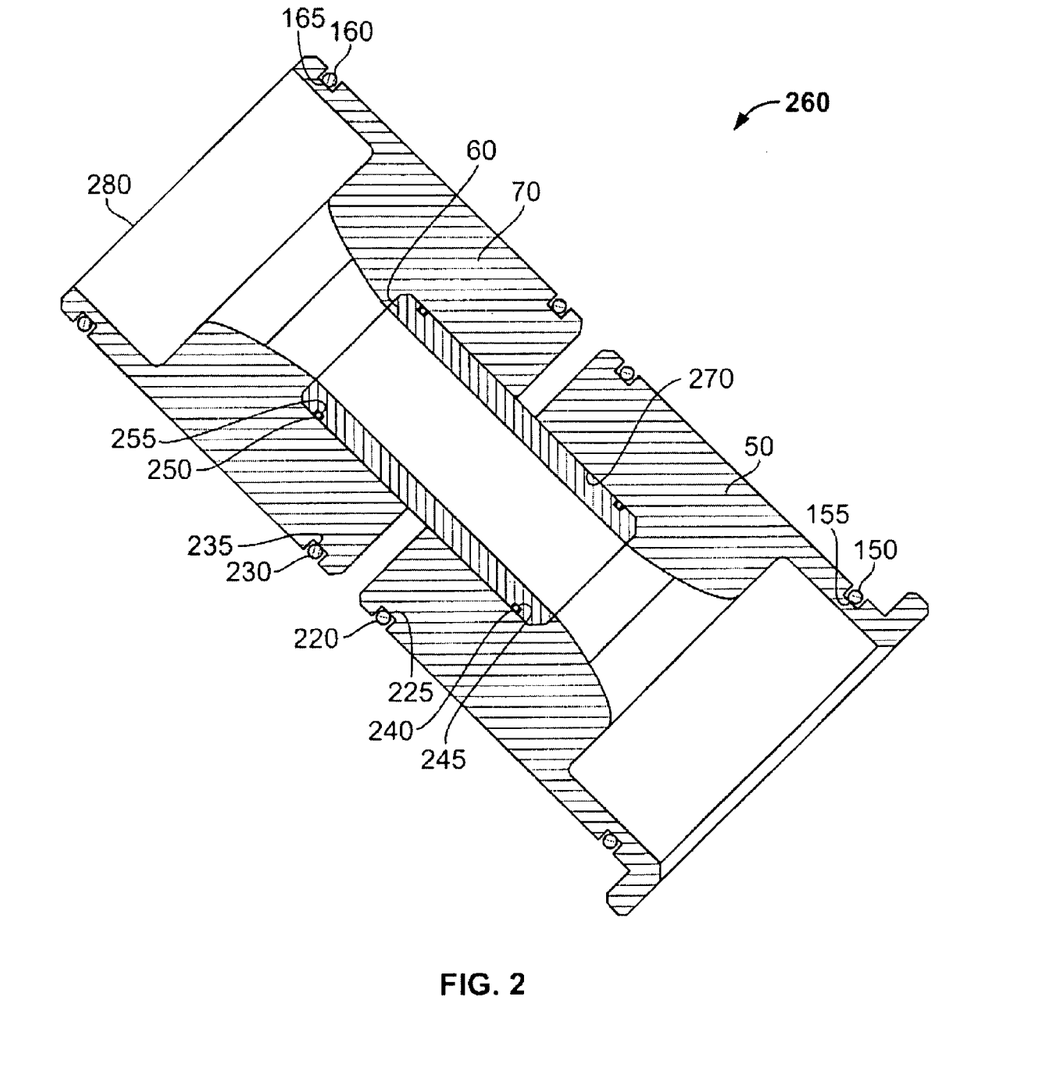
FIG. 2 is an assembly of a portion of the system of FIG. 1.

With reference to FIGS. 1 and 2, assembly of the system 10 is described. FIG. 2 shows an assembly 260 of the first and second pistons 50, 70 and the sleeve 60 and associated sealing members 150, 160, 220, 230, 240, and 250. As shown, the sealing members 150-160 and 220-250 are disposed in their respective grooves 155, 165, 225, 235, 245, and 255, respectively. In some implementations, internal contours of the sleeve 60 may be greased with high temperature (HT) grease. The sleeve 60 may be inserted into a cavity 270 inside the first piston 50. The second piston 70, with the sealing members 160 and 230 disposed in respective grooves 165 and 235, respectively, is placed over the sleeve 60 extending from the first piston 50. The sleeve 60 may be formed from a metal, metal alloy, a Teflon coated material, or any other suitable material that does not bond with the cementitious material when the cementitious material cures within the system 10 under the applied conditions, e.g., temperature and pressure (described in more detail below). In some instances, the sleeve 60 may be formed from a group of materials known as "superalloys" or "high-performance alloys". For example, the sleeve 60 may be machined or otherwise formed from a Hastelloy® alloy produced by Haynes International, Inc., of 1020 W. Park Avenue, Kokomo, Ind. An exterior surface of the sleeve 60 may be coated with a grease, for example, to facilitate relative movement of the sleeve 60 and the first and second pistons 50, 70. The first end-cap 30 may be threadably coupled to a bottom portion of the pressure vessel 20 with the sealing member 180 disposed in the groove 185.

The assembly 260 may be inserted into the pressure vessel 20 until the first piston 50 abuts the first end-cap 30. The slurry of the cementitious material may be poured into the interior volume 80 through an opening 280 formed in the second piston 70 until the entire interior volume 80 is filled. The second end-cap 40, with the sealing member 170 disposed in the groove 175, may be threadably coupled to the pressure vessel 20 to form a pressure-tight seal. Although the first and second end-caps 30 and 40 are described being threadably coupled to the pressure vessel 20, in other implementations, the first and second end-caps 30 and 40 may be coupled to the pressure vessel 20 in other ways, such as with one or more clamps, one or more fasteners, or any other suitable coupling method. The coupled first and second end-caps 30 and 40 may include sealing elements To better homogenize the slurry of cementitious material and/or to better ensure that the slurry fills all of the contours of the interior volume 80, surface 290 of the first end-cap 30 may be placed on a flat, horizontal surface, and a glass rod or any other suitable object may be used to puddle the cementitious material during or after the slurry is being poured. Foamed slurries may be transferred at pressure into the interior volume 80 through a port 300 extending through the first end-cap 30.

The system 10 may be enclosed in a heating jacket, inserted into an autoclave, or a cooling chamber to cure the cementitious material at a desired temperature. A curing pressure of up to 60,000 psi or greater may be applied and transmitted to the cementitious material by pumping a fluid, such as water, oil or any other fluid having a density less than a density of the slurry. The fluid may be pumped using a syringe pump, centrifugal pump or any other device operable to provide a desired pressure as the cementitious material cures. The pressure and temperature applied to the cementitious material may be controlled independently using a pressure controller and a temperature controller, respectively, or by a single controller operable to control both the pressure and temperature. In some implementations, the controller may be manual. In other implementations, the controller may be automated that automatically maintains the temperature and/or pressure at a setpoint or alters the temperature and/or pressure over time according to a defined program.

The slurry of cementitious material may be allowed to cure under downhole conditions for a selected period of time after which the mechanical properties of the solid specimen can be determined. After the lapse of the selected time period, the pressure applied via port 120 may be maintained. To apply tensile loading to the cured sample 110, pressurized fluid may be applied through the port 195. The pressurized fluid enters the interstitial region 210 at the interface between the first and second pistons 50, 70. The pressurized fluid works to separate the first and second pistons 50, 70 and create tensile stress in the sample 110. The pressure of the fluid may be gradually increased by continuing to pump the fluid at a constant rate. In other implementations, the fluid may be pumped at a non-constant rate.

Pressure of the pressurized fluid may be controlled in a similar manner as the fluid used to pressurize the cementitious material during curing. For example, a controller may be programmed to control an amount of the pressurized fluid injected based on the rate of change of pressure or by the volume flow rate of the pressurized fluid. One or more strain gauges may be incorporated into the sleeve 60. In some implementations, the one or more strain gauges may be run along a length of the sleeve 60. For example, in some instances, one or more strain gauges may be incorporated into an internal diameter of the sleeve 60. Alternately, a strain measurement may be obtained by mounting a displacement measuring device, such as a linear variable differential transformer (LVDT) or one or more strain gauges 22, to measure movement of either of the first or second pistons along an axial direction of the system 10; movement between both of the first and second pistons 50, 70 along the axial direction of the system 10; or a movement between the sleeve 60 and at least one of the first or second pistons 50, 70 along an axial direction of the system 10. Still further, in other instances, a strain measurement may be obtained by embedding one or more bi-axial strain gauge in the slurry itself. Additionally, in other implementations, strain measurements may be obtained by optical strain measurements.

Strain may be calculated using the initial position of the first and second pistons 50, 70 within the system 10 when displacement is measured along with the amount of displacement. Stress may be calculated or otherwise obtained from pressure or load readings indicated by the pump controller, a pressure transducer, one or more load cells, one or more force transducers; or from measurement obtained from any other suitable device. Additionally, a piezoelectric device may be disposed in an interfacial region 310 between a flanged portion 100 of the sample 110 and an annular surface of the adjacent piston 50 or 70 to get a more accurate measurement of the force being applied to the sample 110. A piezoelectric device may be operable to obtain load measurement data.

The tensile stress may be calculated using the initial cross-sectional area of the central portion 90 of the sample 110. As indicated above, in some implementations, the central portion 90 may have a uniform cross-section. One or more strain gauges may be mounted circumferentially in the sleeve 60. Data obtained from the one or more strain gauges may be used to obtain Poisson's ratio. Stress and strain measurements may be recorded with respect to time using a data acquisition system. The acquired data may be analyzed to interpret Young's modulus.

When the tensile stress within the cementitious material under testing exceeds its Ultimate Tensile Strength, the sample 110 breaks somewhere in the region of the central portion 90, e.g., at a location in the uniform cross section. This fracture of the sample 110 may be indicated by a sudden drop of measured stress on the stress strain curve, or by a sudden decrease in fluid pressure of the fluid being injected through the port 195. Alternatively, the fracture of the sample 110 may be interpreted by a sudden increase in the fluid pressure applied via the port 195 if the pressure is locked in or a sudden displacement of volume from the system 10 if the pump for applying the hydraulic pressure to the cementitious material is operated in a constant volume mode. An inflection point on a graph of the applied fluid pressure in either of the above-mentioned situations would give an indication of the stress at which the sample failed under tension.

Figure 3:
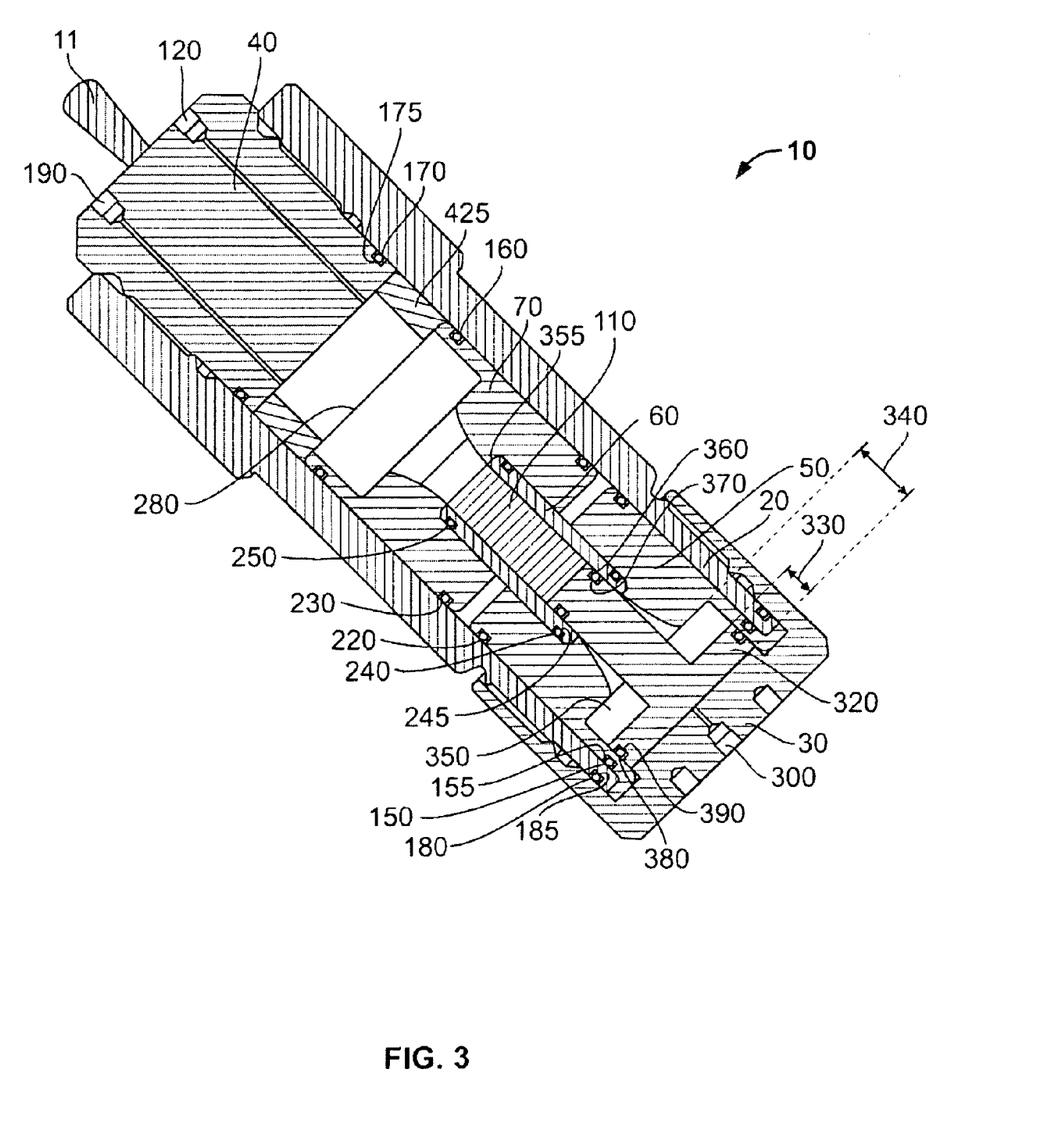
FIG. 3 is another cross-sectional view of the system of FIG. 1 in which the system is configured for a shear bond strength test.

According to another implementation, FIG. 3 shows the system 10 for use in performing a shear bond strength test of the cementitious material. The shear bond strength test may be used to determine the load required to shear the cementitious material that has cured under downhole conditions from a material in contact with the cementitious material as the cementitious material cured. The shear bond test may be performed by measuring the load required to displace the cementitious material allowed to cure within the sleeve 60 relative to the sleeve 60. Although the system shown in FIG. 3 is illustrated without port 195 and passageway 200, the port 195 and passageway 200 may be included.

The shear bond strength test may be performed by incorporating a third piston 320. The sleeve 60 may be formed from a metal or any other desired material for which a shear bond measurement is desired. In some implementations, the sleeve 60 may be machined out of a metal alloy of interest. For example, the metal alloy may be any alloy used to form a wellbore casing. These materials are of particular interest in order to evaluate the strength of the bond formed between the cured cementitious material and the bordering casing used downhole. In some implementations, the metal of the sleeve 60 may be sand blasted to produce a uniform, clean surface; coated with one or more materials to improve bonding; corroded; mill varnish coated; coated with drilling fluid; or any other substance typically found in wellbores that may affect the shear bond. Thus, the evaluation of the effects these materials may have under downhole conditions of pressure and temperature may be evaluated.

The third piston 320 may be disposed in the flange portion 100 of the first piston 50, with a portion of the piston extending into the sleeve 60. Thus, the third piston 320 defines an end of the central portion 90 formed by the sleeve 60. A thickness 330 of the third piston 320 is smaller than a thickness 340 of the flange portion 100 defined by the first piston 50 so that a gap 350 is formed. Thus, the third piston 320 may be displaced longitudinally relative to the first piston 50.

Slurry of cementitious material is poured into the sleeve 60 up to rim 355 of the sleeve forming a shape defined by the sleeve 60 and the third piston 320. The cementitious material is cured in place inside the sleeve 60 under desired conditions of temperature and pressure, as discussed above. Thus, the cementitious material forms the shape of the interior defined by the sleeve 60 and the third piston 320. The top part of the slurry is exposed to hydraulic pressure exerted by a fluid injected via port 120. A sealing member 360 may be mounted in a groove 370 on a portion of the third piston 320 extending into the sleeve 60. The sealing member 330 provides a seal to prevent or substantially reduce the pressurized slurry in the sleeve 60 from entering the flange portion 100 formed by the first piston 50. The slurry of cementitious material is permitted to cure under desired conditions, temperature and pressure, forming the sample 110. As mentioned above, some implementations may be used at high temperatures that may be detrimental to some sealing materials, such as polymeric seals. Accordingly, some implementations may utilize high temperature sealing materials, such as metals to form a metal-to-metal seals, for one, more than one, or all sealing members in the system 10.

After the slurry is cured in place, fluid pressure may be introduced from the port 300 in the first end-cap 30, creating a compressive force on the third piston 320. The third piston 320 transfers the force from the fluid pressure to the sample 110. A sealing member 380 disposed in corresponding groove 390 formed in the third piston 320 isolates the pressurized fluid introduced into the chamber via the port 300 from the flange portion 100 formed by the first piston 50. This enables a more accurate measurement of the force transmitted by the third piston 320 to the sample 110 cured in place. The port 300 may be coupled to a constant volume pump or any other similar type of pump that can be used for the tensile testing method, described above.

As the fluid pressure behind the third piston 320 is increased, the force transmitted to the sample 110 also increases. At a particular pressure, the sample 110 separates from the sleeve 60. The pressure at which separation occurs may be determined in a similar fashion as previously explained in the context of determining ultimate tensile strength, e.g., identifying a sudden drop of pressure through the port 300 or an increase in the volume-occupied by the pressurized fluid as a consequence of the breakage of the bond between the sample 110 and the sleeve 60. Curing pressure, if maintained, would also show a sudden spike as the shear bond breaks.

As the fluid pressure applied through the port 120 is maintained constant, for example, by using a constant volume pump, the fluid pressure applies a force on surfaces of the second piston 70 and the sample 110. The second end-cap 40 transmits a counter force as the fluid pressure introduced via the port 300 acts on the third piston 320 to break the shear bond. The spacer ring 425 may be inserted between the second piston 70 and the second end-cap 40 to secure the assembly 260 in position during the shear bond strength test.

Figure 4:
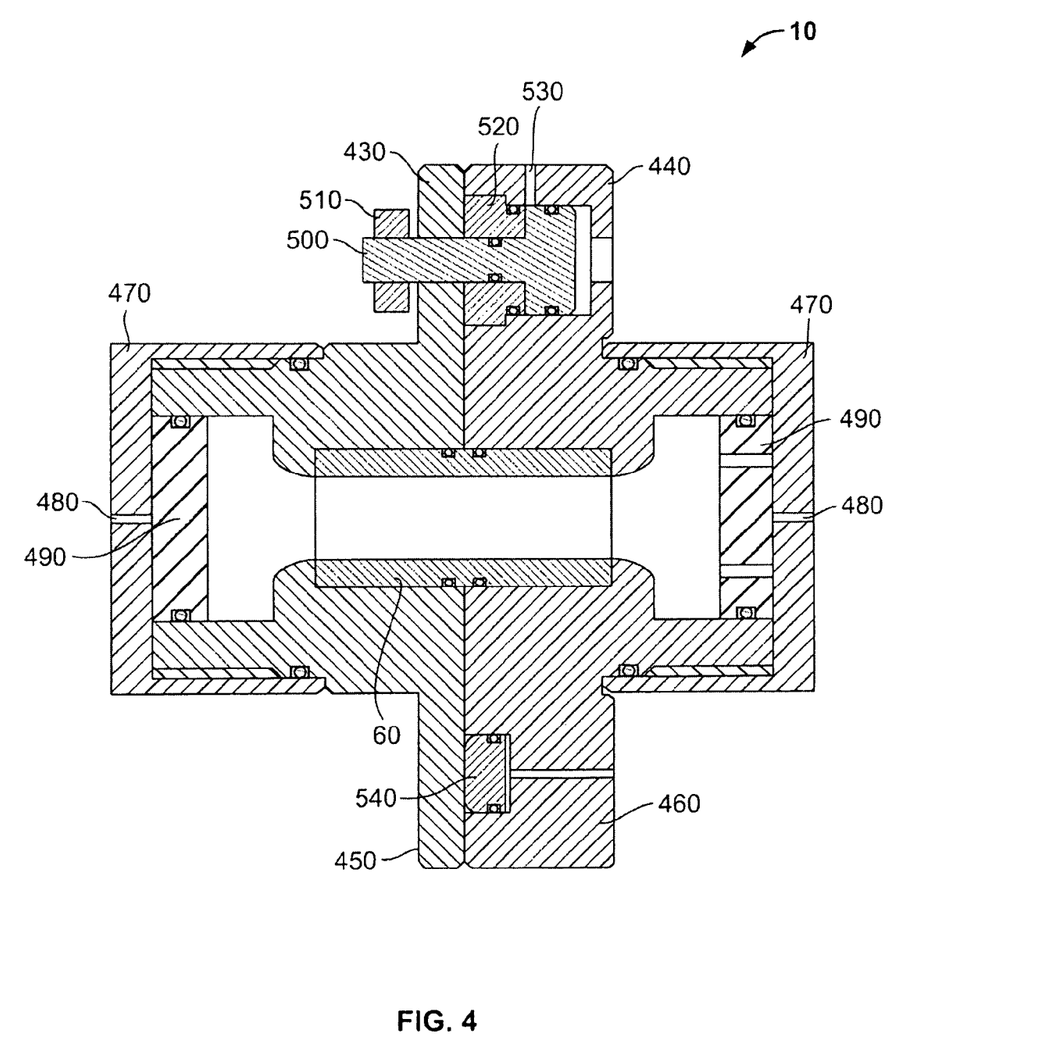
FIG. 4 is a cross-sectional view of a system according to other implementations.

Referring to FIG. 4, another implementation of the system 10 is shown. The system 10 includes a first half 430 and a second half 440. The first and second halves 430, 440 include flanges 450, 460, respectively. An end-cap 470 is coupled to each of the first and second halves 430, 440. In some implementations, the end-caps 470 are threadably coupled to the first and second halves 430, 440. A sample may be formed within the interior volume 80 defined by interior contours of the first and second halves 430, 440. A curing pressure may be applied to the sample via pressure ports 480 on the end caps 470 with the hydraulic pressure being mechanically applied via opposing pistons 490. In other implementations, the pistons 490 may be eliminated and curing pressure may be applied directly to the sample via hydraulic pressure applied to the flanged ends of the sample.

The first and second halves 430, 440 may be held in place hydraulically by three stemmed clamp pistons 500 provided at a flange interface between the flanges 450, 460, located on a common circumference and spaced apart at equal angular displacements. In other implementations, fewer or more clamp pistons may be used and the clamp pistons 500 need not be separated by equal angular displacements. Stop nuts 510 are threaded onto stems of the clamp pistons 500. The clamp pistons 500 may be held in place with threaded and sealed retaining rings 520.

When pressurized fluid is introduced into the space between the retaining ring 520 and the clamp piston 500 via a pressure port 530, the clamp piston 500 is raised off the retaining ring 520 until the stop nuts 510 contact an exterior surface of the flange 450. The resultant clamping force acts opposite to the parting force induced by pressurizing the interior volume 80, and therefore holds the first and second halves 430, 440 together.

Tensile stress may be applied to a sample formed within the interior volume 80 by pressurizing three parting pistons 540 located on a common circle about the flange interface at equal angular displacement. In other implementations, more or fewer parting pistons 540 may be used, and the parting pistons 540 need not be placed at equal angular displacements. When exposed to a pressurizing fluid, the parting pistons 540 apply a force between the first and second halves 430, 440 in a direction opposite the direction of the force applied by the clamping pistons 500.

A number of implementations have been described. Nevertheless, it will be understood that various modifications may be made without departing from the spirit and scope of the disclosure. Accordingly, other implementations are within the scope of the following claims.

What is claimed is:

1. An apparatus comprising:
a housing defining an interior chamber;
a first piston adjacent a second piston in the interior chamber and forming an interstitial region between the first piston and the second piston, the first piston and second piston moveable relative to each other in the interior chamber;
an interior volume defined by the first piston and second piston, the interior volume having a central portion at a region proximate the interstitial region and enlarged portions at opposite ends of the central portion, a cross-section of the enlarged portions being larger than a cross-section of the central portion; and
a first port opening in the interior chamber proximate the interstitial region, wherein the first port is operable to introduce fluid pressure to the interstitial region to apply a separation force operable to separate the first piston and the second piston.

2. The apparatus of claim 1 further comprising a sleeve disposed in the central portion of the volume.

3. The apparatus of claim 2, wherein the sleeve comprises an interior passageway having a constant cross-section.

4. The apparatus of claim 1 further comprising a temperature control device operable to control a temperature of the interior chamber.

5. The apparatus of claim 1 further comprising:
a second port operable to introduce fluid pressure into the interior chamber; and
a pressure control device operable to control a pressure of the interior chamber by adjusting the fluid pressure introduced via the second port.

6. An apparatus comprising:
an enclosure defining an interior chamber;
a first piston disposed in the interior chamber and having a first interior cavity comprising a narrow portion and an enlarged portion;
a second piston disposed in the interior chamber adjacent the first piston at an interstitial region and having a second interior cavity comprising a narrow portion and an enlarged portion, the first piston and second piston moveable relative to each other in the interior chamber and the first interior cavity and second interior cavity arranged such that the narrow portions are adjacent and in fluid communication with each other at the interstitial region; and
wherein the enclosure defines a first opening proximate the interstitial region for introducing fluid pressure into the interior chamber, the fluid pressure operable to apply a separation force to the first piston and the second piston.

7. The apparatus of claim 6 further comprising a pressure control device operable to control a pressure of the enclosure by adjusting the fluid pressure introduced via a second opening in the enclosure.

8. The apparatus of claim 6 further comprising a temperature control device operable to control a temperature within the enclosure.

9. A method of curing and testing a cementitious material under desired conditions of temperature and pressure comprising:
introducing a slurry of cementitious material into an interior volume defined by a first member and a second member, the first member and second member moveable relative to each other;
applying a desired temperature and a desired pressure to the slurry as the slurry cures; and
applying a fluid pressure to generate a tensile stress in the cured cementitious material while maintaining the cured cementitious material at the desired temperature and pressure by applying the fluid pressure to an interstitial region between the first member and the second member to apply a separation force to the first member and the second member, wherein introducing the slurry into the interior volume comprises introducing the slurry into the interior volume defined by interior contours of the first member and the second member while the first member and the second member are adjacent each other at an interstitial region.

10. The method of claim 9, wherein applying the fluid pressure to generate the tensile stress in the cured cementitious material while maintaining the cured cementitious material at the desired temperature and pressure comprises applying the fluid pressure to a third member moveable relative to the first member to press the cured cementitious material relative to a cylindrical member in which the cured cementitious material is disposed.

11. The method of claim 9, wherein applying the desired temperature and the desired pressure to the slurry as the slurry cures comprises applying a temperature and a pressure expected to be experienced by the cementitious material downhole.

12. The method of claim 9 further comprising sensing a characteristic indicative of the tensile stress.

* * * * *